United States Patent [19]

Bodai

[11] 4,351,328

[45] Sep. 28, 1982

[54] SIMULTANEOUS RESPIRATION AND ENDOTRACHEAL SUCTIONING OF A CRITICALLY ILL PATIENT

[75] Inventor: Balazs I. Bodai, Sacramento, Calif.

[73] Assignee: Sontek Industries, Inc., Dallas, Tex.

[21] Appl. No.: 204,841

[22] Filed: Nov. 7, 1980

Related U.S. Application Data

[63] Continuation-in-part of Ser. No. 134,528, Mar. 27, 1980, abandoned.

[51] Int. Cl.³ .................. A61H 31/00; A61M 25/00
[52] U.S. Cl. .......................... 128/202.16; 128/349 B
[58] Field of Search ............... 128/10, 200.26, 201.26, 128/201.28, 205.19, 203.24, 203.21, 205.21, 206.22, 206.29, 348, 349 R, 276–278, 213, 222, 207.14, 207.15, 207.16, 202.13, 202.16

[56] References Cited

U.S. PATENT DOCUMENTS

| | | |
|---|---|---|
| 2,023,267 | 12/1935 | De Saint Rapt et al. |
| 2,127,215 | 8/1938 | Gwathmey |
| 2,537,674 | 1/1951 | Johnson |
| 2,584,450 | 2/1952 | Holt et al. |
| 2,638,096 | 5/1953 | Waldhaus ............ 128/207.14 |
| 2,710,623 | 6/1955 | Kolos |
| 2,862,498 | 12/1958 | Weekes |
| 2,912,982 | 11/1959 | Barsky |
| 3,067,425 | 12/1962 | Colley |
| 3,097,646 | 7/1963 | Scislowicz |
| 3,100,498 | 8/1963 | Gibson, Jr. |
| 3,236,236 | 2/1966 | Hudson ................ 128/207.17 |
| 3,477,438 | 11/1969 | Allen et al. |
| 3,670,726 | 6/1972 | Mahon et al. |
| 3,730,179 | 5/1973 | Williams |
| 3,853,127 | 12/1974 | Spademan |
| 3,896,810 | 12/1975 | Akiyama ................ 128/276 |
| 3,902,489 | 9/1975 | Carter |
| 3,937,220 | 2/1976 | Coyne |
| 4,000,739 | 1/1977 | Stevens |
| 4,022,219 | 5/1977 | Basta |
| 4,048,995 | 9/1977 | Mittleman |
| 4,106,491 | 8/1978 | Guerra |
| 4,149,535 | 4/1979 | Volder |
| 4,152,017 | 5/1979 | Abramson |
| 4,177,814 | 12/1979 | Knepshield et al. |
| 4,240,417 | 12/1980 | Holever ................ 128/207.15 |
| 4,291,691 | 9/1981 | Cabal et al. ........... 128/207.14 |

OTHER PUBLICATIONS

Product Literature (6 pages) for a Trach Care Tracheal System offered by Efficon Corporation, Renton, Washington.
Untitled, undated paper (Beginning "Background", Including pp. 1–6).
Naigow & Powaser, "The Effect of Diff. Endotracheal Suction Proc." etc., Heart & Lung, pp. 808–816, Sep.-/Oct. 1977, vol. 6, No. 5.
Millen & Grenvik, "Hemodynamic Response" etc., Critical Care Medicine, pp. 85–90, vol. 2, No. 2, Mar.-/Apr. 1973.
Adlkofer & Powaser, "The Effect of Endotracheal Suctioning etc." Heart & Lung, pp. 1011–1014, Nov./Dec., 1978, vol. 7, No. 6.
Hemaguet Arterial/Venous Catheter Introducer Product Literature (2 pages).
Superior Plastic Products' Continuous Ventilating Suction System Product Literature (2 pages).

*Primary Examiner*—C. Fred Rosenbaum
*Attorney, Agent, or Firm*—Limbach, Limbach & Sutton

[57] ABSTRACT

A method and apparatus for accomplishing endotracheal suctioning of a patient without having to disconnect the patient from a respirator. A suctioning tube is positioned in the tracheal tube through a wall of the respirator tubing set, in a manner maintaining the integrity of the respiration system. The technique is particularly useful for maintaining positive end expiratory pressure without interruptions during suctioning.

24 Claims, 11 Drawing Figures

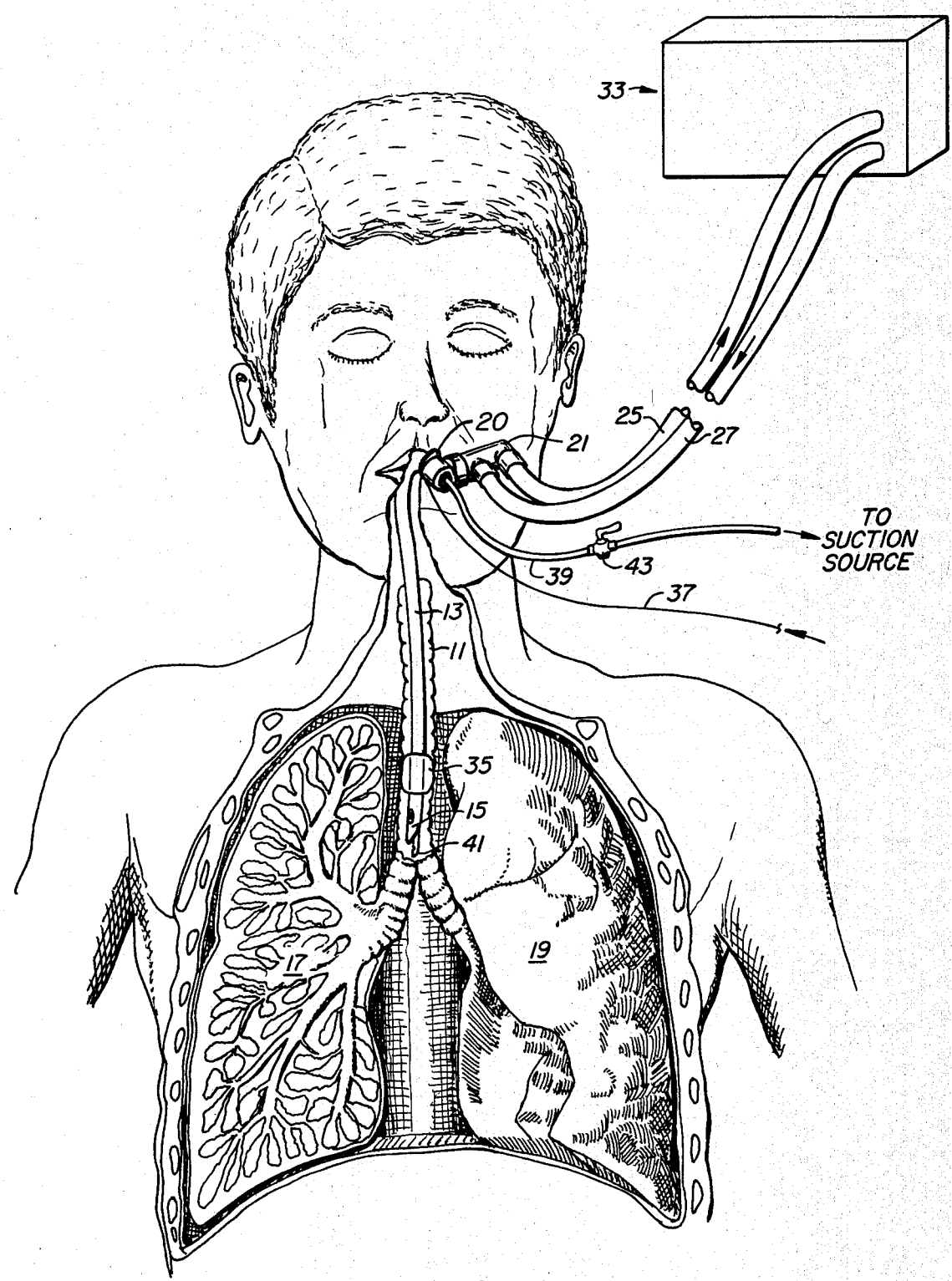
FIG._1.

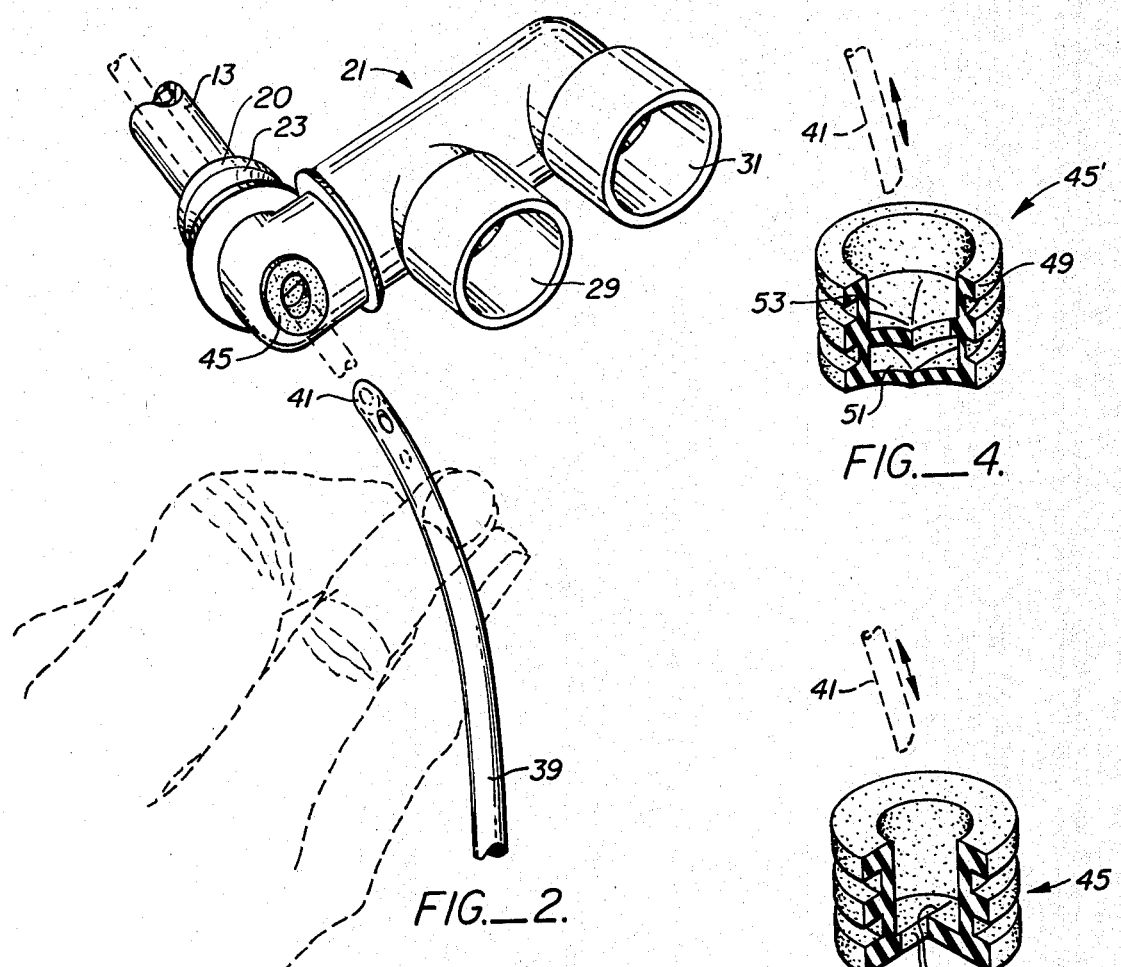
FIG._2.
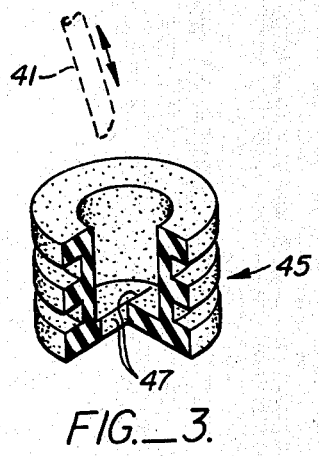
FIG._4.
FIG._3.
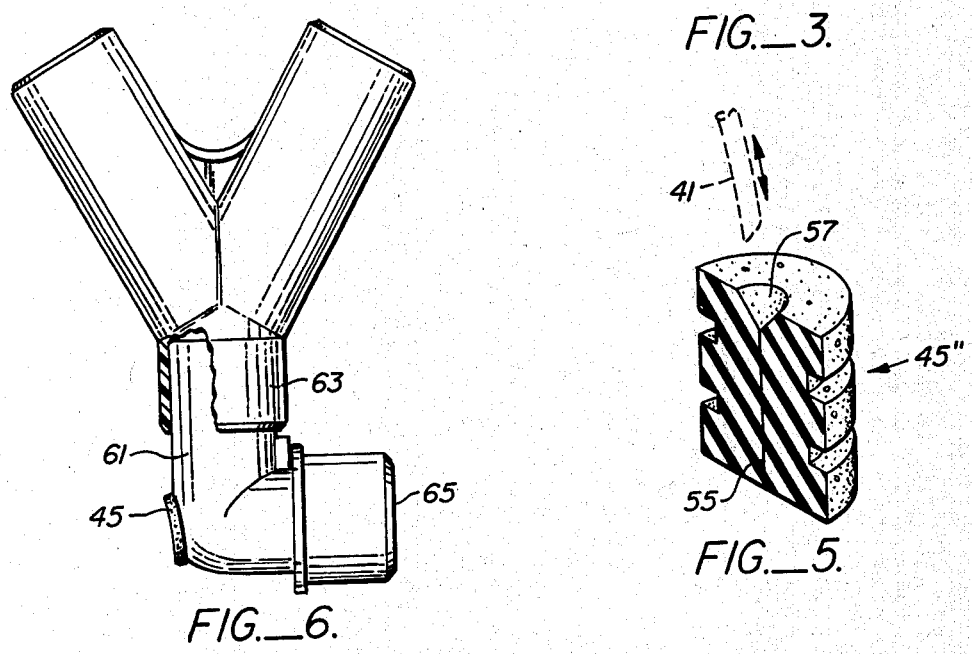
FIG._6.
FIG._5.

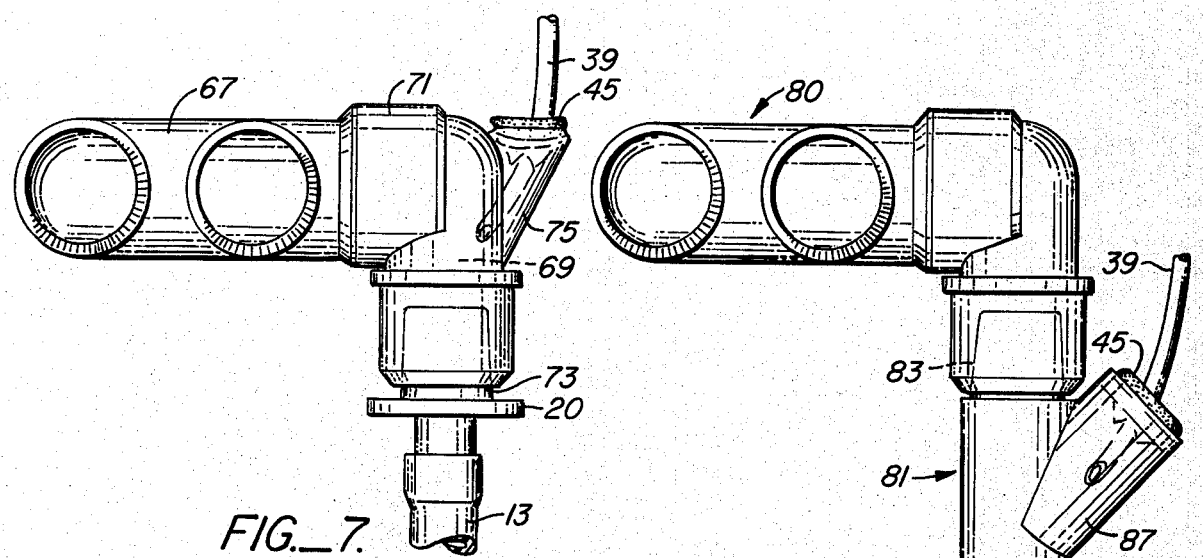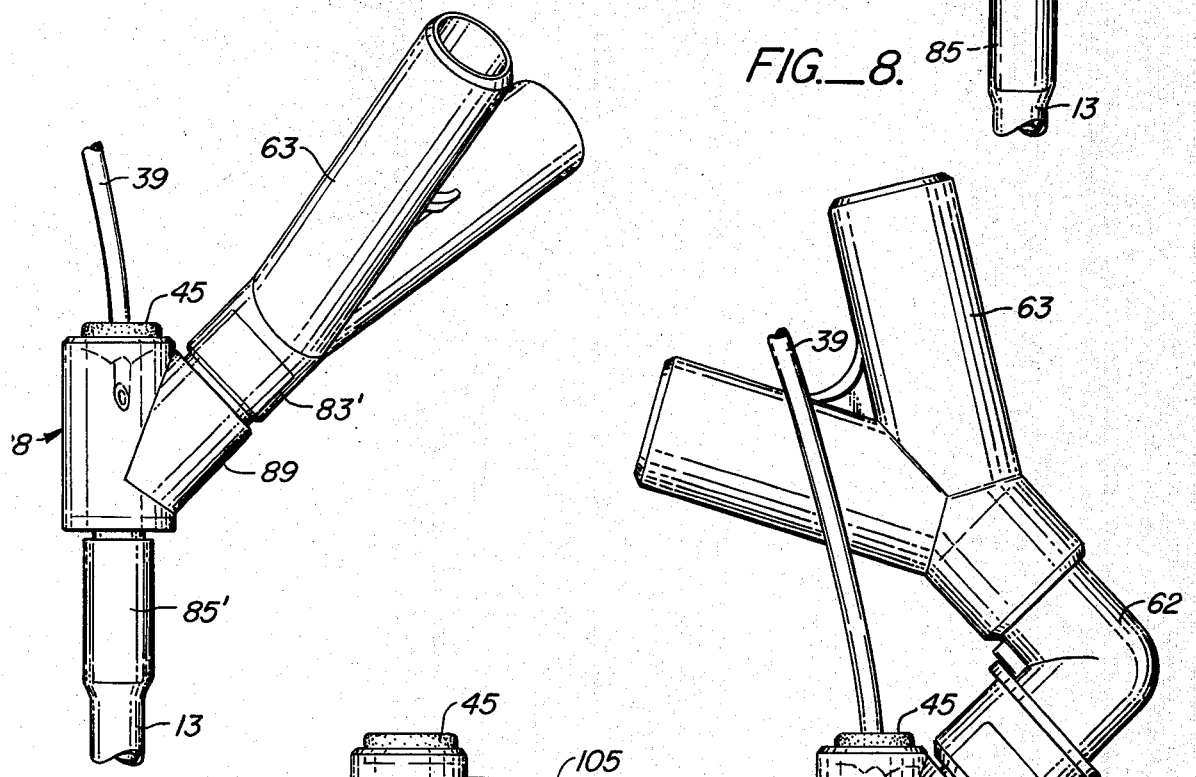

4,351,328

SIMULTANEOUS RESPIRATION AND ENDOTRACHEAL SUCTIONING OF A CRITICALLY ILL PATIENT

CROSS-REFERENCE TO RELATED APPLICATION

This application is a continuation-in-part of copending application Ser. No. 134,528, filed Mar. 27, 1980 now abandoned.

BACKGROUND OF THE INVENTION

This invention relates generally to the care of human patients, and more specifically to a method and apparatus for performing endotracheal suctioning of a patient who is connected to a respirator machine.

Ventilation of patients by connecting them to a respirator is a widespread practice to aid in their breathing when critically ill, such as during or immediately following an operation. A typical respirator provides a breathing gas for the patient having a high level of oxygen in one tube and receives back in another tube the gases exhausted by the lungs of the patient. These two tubes are joined together at a manifold position that is as close to the point of entry to the patient as possible. A single additional tube positioned into the trachea of the patient, either directly or through the nose or mouth, is connected to the manifold. A principal goal of such a ventilation technique is to maintain a high level of blood oxygenation in the patient without the heart and lungs having to work excessively hard.

A patient so connected to a respirator requires periodic removal of fluid from the trachea. The present technique as widely practiced in hospitals is to disconnect the respirator hoses from the patient, and then to insert through the tracheal tube a separate, small-diameter suctioning tube which is used to remove the fluids from the trachea. During this periodic process, some temporary breathing assistance is provided, but not of the quality or quantity as provided by the respirator. This interruption necessarily results in the oxygen level of the blood to decrease, and for the heart and lungs to have to work harder, a problem with many critically ill patients. Much has been written about the solution to this problem, typical suggestions being to hyperinflate the lungs before and/or after the suctioning process, and varying the parameters of the suctioning operation, including the size of the suctioning tube, the suctioning pressure, its duration, etc. But none of these techniques result in maintaining the same level of breathing assistance as when the patient's connection to the respirator is uninterrupted.

The use of positive end expiratory pressure (PEEP) has gained wide popularity in the management of the respiratory status of critically ill patients. Generally, this known technique maintains through an appropriate respirator a slightly positive gaseous pressure to the patient at all times. The basic advantage of this technique is that it allows a lower concentration of oxygen to be provided to the patient in order to maintain an adequate level of blood oxygenation. It is thought that this is due to the fact that the positive pressure maintains a larger number of the patient's lung alveoli open during the respiratory support, thereby increasing the effective lung area of ventilation and decreasing ventilation/perfusion defects. Although there is some controversy as to the effect of interrupting such a positive pressure for various nursing maneuvers such as suctioning, changing tubing, etc., empirical data tends to suggest that the interruption of the positive pressure leads to an immediate effect in a sudden collapse of lung alveoli. This data also suggests that it takes a substantial amount of time after such an interruption for the positive pressure to restore the lung alveoli to their open state.

Therefore, it is a primary object of the present invention to provide a method and apparatus for endotracheal suctioning of a patient which eliminates the foregoing disadvantages associated with existing interruptions of respiratory support to the patient.

SUMMARY OF THE INVENTION

This and additional objects are accomplished by the various aspects of the present invention wherein, briefly and generally, endotracheal suctioning of a patient is accomplished without interrupting the connection of a patient to a respirator. An opening is provided in a wall in the fluid conduit between the patient and the respirator at a location very close to entry into the patient. That opening is sealed in a manner to permit insertion of a suctioning tube therethrough without opening the respiratory supply system to the atmosphere. Once the suctioning is accomplished, the suctioning tube is removed by pulling back through the seal which reseals itself. The respiratory supply system remains isolated from the atmosphere during the suctioning operation and thus allows the patient to be maintained on positive end expiratory pressure without interruption. The technique maintains the advantage of allowing the person performing the suctioning to vary the depth of insertion of the suctioning tube and to otherwise control its position.

Additional objects, advantages and features of the various aspects of the present invention will become apparent from the following detailed description of its preferred embodiments, which should be taken in conjunction with the accompanying drawings.

BRIEF DESCRIPTION OF THE DRAWINGS

FIG. 1 generally illustrates the improved suctioning technique of the present invention on a patient who is connected to a respirator;

FIG. 2 shows a commercially available manifold of the system of FIG. 1 that has been modified to include, in one form, the present invention;

FIGS. 3, 4 and 5 are different types of sealing members for use with the embodiment illustrated in FIGS. 1 and 2;

FIG. 6 shows the installation of one of the seals of FIGS. 3-5 in another existing commercial manifold;

FIG. 7 illustrates a different installation of a seal of FIGS. 3-5 in the commercially available manifold of FIGS. 1 and 2;

FIGS. 8, 9 and 10 show embodiments of the present invention wherein a connector piece is used in conjunction with commercially available manifolds; and FIG. 11 illustrates a connector piece of the type shown in FIGS. 8-10 with added mechanical features.

DESCRIPTION OF THE PREFERRED EMBODIMENTS

Referring initially to FIG. 1, the most common type of connection of a patient to a respirator is shown. Within the patient's trachea 11 is installed through the mouth an endotracheal tube assembly 13 that is commercially available. End 15 of the tube 13 is opened and generally positioned in the trachea 11 in the vicinity of where the trachea branches into the two lungs 17 and 19. An opposite end of the endotracheal breathing tube 15 is connected to a manifold 21, shown in more detail in FIG. 2. The endotracheal tube 13 is connected through a separate attachment piece 20 to a first port 23. Flexible breathing hoses 25 and 27 (FIG. 1) are connected respectively to second and third ports 29 and 31 of the manifold 21 (FIG. 2). Opposite ends of the hoses 25 and 27 are connected to a respirator 33 of an available type. The respirator 33 provides through a hose 27 to a patient a gas mixture high in oxygen content. The hose 25 receives the expelled air through the lungs of the patient and carries it to the respirator 33.

The combination of the manifold 21 and the hoses 25 and 27 are disposable plastic parts sold as a manifold set, one such set never being used for more than one patient. Valves, regulators and the like are associated with the hoses of a manifold set are not shown in FIG. 1. Such a manifold set in combination with a separately sold tracheal tube assembly 13 provides a complete conduit between the lungs of the patient and the respirator 33.

Commercially available tube assembly 13 includes a balloon-like element 35 attached near its free end that serves a purpose of blocking the trachea when inflated, except for the passage within the interior of the tube 13. A small, flexible tube 37 is generally supplied as part of the tracheal tube assembly 13 that communicates with the balloon-like element 35 for inflation or deflation thereof.

The foregoing describes with respect to FIGS. 1 and 2 basic elements of a commonly used respirator system. The improvement of the present invention is the insertion of a suctioning tube 39 into the trachea 11 of the patient through the tracheal tube 13 without having to disconnect the respirator 33 from the patient. A free end 41 of the suctioning tube 39 is generally extended slightly beyond the end 15 of the tube 13 in order to remove fluid accumulated in that region. It is preferable that the suctioning tube 39 contain a valve 43 in its path, which allows the operator to selectively open or close the conduit within the tube 39. An opposite end of the tube 39 is connected to a standard available suctioning source (not shown). The suctioning tube may be removed from the trachea tube after each suctioning operation, or alternatively may be left within the trachea tube between times with the valve 43 closed.

Referring primarily to FIG. 2, the structure and technique which makes simultaneous suctioning and respiration possible is generally illustrated. An opening is provided in a side wall of the manifold 21 that would otherwise destroy the closed respiratory system that is necessary, except that a seal 45 is positioned therein to normally close the opening. The seal 45 is structured, however, to open upon the urging of the end 41 of the suctioning tube 39 to receive the tube and allow it to be pushed down into the trachea of the patient through the tracheal tube 13. The seal 45 is in the nature of a valve which receives the suctioning tube 31 and forms a substantial seal around it when installed in the opening of the manifold 21. Similarly, when the suctioning tube 39 is removed all the way out of the respiratory path by complete removal from the opening, its seal 45 reseals to maintain the integrity of the closed respiration path. The seals are automatically made upon insertion and removal of the suctioning tube, without any further manipulation being necessary. Each is resiliently biased to close on itself or on a tube positioned through it. The suction tube is a commonly available plain tubing that is available in pre-sterilized packages, more complicated assemblies such as those using a surrounding envelope and hard plastic end fitting for connection to the ventilation conduit being unnecessary.

This technique is to be compared with one presently used technique wherein, for instance, the manifold 21 would be disconnected from the tracheal tube 13, thus interrupting the respiratory support of the patient, while the suctioning tube is inserted into the tracheal tube 13 for the necessary periodic suctioning of the patient.

FIG. 3 illustrates a particular form of the seal 45. It is made in a cup-like shape of resilient rubber material or some equivalent plastic compound. In this specific form, a single slit 47 is provided in the bottom of the sealing member 45 and normally remains closed but is opened by spreading apart the edges of the slit 47 upon insertion of the suctioning tube end 41. Upon removal of the tube 39, the opening 47 again closes under the influence of the material's own resiliency.

Another sealing structure 45' is illustrated in FIG. 4. A cylindrical shell 49 that is held by the opening within the manifold 21 has two thinner pieces of resilient rubber-like material 52 and 53 spanning the opening within the cylincrical shell 49. Each of the layers 51 and 53 is provided with three slits, in this specific embodiment, extending halfway across the opening within the sleeve 4 and oriented at approximately 120 degrees with respect to each other. The slits of one of the layers 51 or 53 is angularly displaced with respect to those of the other. The result is a double-layered seal that prevents the passage of gases therethrough when there is a pressure differential across the seal 45'. It also provides a good seal when the suctioning tubing 39 is positioned therethrough. When positive end expiratory pressure it utilized in the respiratory system, the positive pressure differential on the inside of the manifold 21 causes the flaps of the layer 53 to be naturally urged against the inside of the flaps of the layer 51, thus providing a natural seal that is made possible by the relative angular displacement of the slits of the two layers 51 and 53. Of course, more than three slits could be provided in each of the layers 51 or 53.

Yet another seal 45" is made of a different material than that of the seals 45 and 45'. The material of the seal 45" is a soft, foam-like plastic material that is compressible to a high degree as well as resiliently returning to its natural state after compressive forces are removed. The seals 45 and 45', on the other hand, are not made of such a compressive material. The seal 45" includes a hole in approximately its center, with an expanded conically shaped hole 57 on an outside surface thereof. The conical aperture opening 57 guides the end 41 of the suctioning tube as it is inserted through the seal 45" by compressing a sealing material to expand the opening 55 to tightly grip the outside of the suctioning tube 59. When the suctioning tube is removed, the seal 45" returns to its closed rest position shown in FIG. 5.

It may in some circumstances be preferable to form a seal of a combination of seals 45 and 45" axially aligned. This relaxes the elastic restoration requirement for the material of seal 45" but still lets it perform a main function of sealing around a suctioning tube when inserted. The seal 45 performs best when no tube 39 is inserted, so the combination takes advantage of the best feature of both.

FIGS. 6 and 7 show the opening and seal of the present invention being installed on present commercially available manifold units of two different manufacturers. Referring to FIG. 6, two pieces 61 and 63 are force-fit one onto the other, but are removable by hand. The piece 61 is modified by drilling a hole opposite a port 65 to which the trachael tube attaches. In this hole is installed a seal of the type discussed previously, such as the seal 45. Providing such an access point for a suctioning tube permits the respirator to remain connected to the patient. A present technique is to remove the piece 63, to which the respirator hoses are attached, from the piece 61 and then to feed a suctioning tube through the piece 61, around its right angle and into the tracheal tube to perform the suctioning operation. Besides the inconvenience of having to feed the tube around the right angle, the patient is, as discussed previously, disconnected from the respirator during this procedure, which, as discussed previously, is highly undesirable.

The manifold of FIG. 7 joins two pieces 67 and 69 by a fluid-tight, rotatable joint 71. A port 73 is adapted for connection through the connector 20 with the tracheal tube 13. It may be preferable in order to least disturb the structure of the available manifold, to place the suctioning tube opening and seal on the side rather than in the wall opposite the port 73. Thus, a section 75 is added along a side of the member 73 in order to carry a seal as discussed previously, such as the seal 45, with an orientation that permits insertion of the suctioning tube 79 substantially parallel to the fluid flow path through the port 73. This prevents having to sharply bend the tube 39.

FIG. 8 shows an application of the present invention that allows using a commercially available manifold 80 without modification. The manifold 80 is like the manifold 21 of FIGS. 1 and 2 except that the seal 45 has not been installed. Rather, the seal 45 is placed in a separate attachment 81 which is connected between the tracheal tube 13, force fitted onto a cylindrical protrusion 85, and an input opening of the manifold 80 which is force fitted onto a protrusion 83 of the part 81. The manifold 80 and tracheal tube 13 are simply attached by force fitting by hand just before use. The piece 81 is hollow and allows air to thus freely pass through it between the tracheal tube 13 and the interior of the manifold 80. The interior of the piece 81 is extended into an abutting portion 87 in which the seal 45 is installed in an end opening. The suctioning tube 39 can thus be urged through the seal 45 and into the tracheal tube 13 through the piece 81.

Shown in FIG. 9 is another attachment or connector 88 that is a variation of the connector 81 of FIG. 8. In this case, the seal 45 is positioned directly opposite the protrusion 85' (corresponds to the protrusion 85 of the connector 81) so that the suctioning tube 39 can be directed head-on down the tracheal tube 13. A protruding stub 83' is adapted for receiving the portion 63 of another type commercial manifold. This is provided on an extension 89 of the main body of the element 88. The protrusions 83 and 83' are designed by their shape to accommodate either of the commercially available manifold pieces shown in FIGS. 8 and 9. The unitary connectors 81 and 88 have the advantage that they simply replace the connector 20 now used and do not require a substantial modification of existing parts, in order to provide the advantages of the present invention.

FIG. 10 shows a combination similar to that of FIG. 9, except that both pieces 62 and 63 of a commercially available manifold are installed on the connector 88. The piece 62 has been removed in the combination of FIG. 9. Of course, other particular combinations of the two connectors and three manifold configurations shown in FIGS. 8 through 10 can be made.

In FIG. 11, a connector base portion 101 is a variation of the pieces 81 and 88 described with respect to FIGS. 8-10. An outlet port structure for connection to a tracheal tube is formed by a separate piece 103 that is journaled within the base 101. Similarly, an outlet port structure for connection to a manifold or air tubes is formed by a separate piece 105 journaled within another opening of the base 101. Free rotation of the pieces 103 and 105, combined with their being oriented to rotate about axes that are substantially orthogonal to each other, provides maximum freedom of ventilation hose and patient relative movement without discomfort to the patient or having to temporarily disconnect the respirator. The pieces 103 and 105 are rotatably held by the piece 101 in some convenient manner that provides a substantial seal against gases passing into or out of their interior. An adjacent groove and ring on the outside surface of each of the pieces 103 and 105 with complementary elements on the interior surface of the piece 101 at each of their orthogonally oriented openings is one structure that provides this.

Another advantage of the techniques described herein is the greater ease with which the suctioning can take place, since disconnection of the respirator and manual respiration during suctioning are avoided. The time required of hospital personnel to do suctioning on a patient connected to a respirator is thus greatly reduced. Also, a patient's trauma often resulting from disconnection of him or her from the respirator is eliminated.

Although the various aspects of the present invention have been described with respect to particular examples thereof, it will be understood that the invention is entitled to protection within the full scale of the intended claims.

I claim:
1. A ventilator system, comprising:
  a conduit adapted to be connected between a trachea tube and a respirator and having an opening in a side wall of said conduit near the trachea tube,
  a length of bendable suction tubing having a valve located a distance from a free end of the tube, said valve being actuatable between positions opened and closed to fluid flow therethrough, and
  means installed in said opening for receiving said free end of the suction tube therethrough for passage through said conduit into the trachea tube, said receiving means being characterized by substantially sealing said opening in the absence of the suction tube being positioned therein, by permitting insertion of the tube therethrough by pushing along its length in a manner to form a substantial seal between the tube and conduit without any further manipulation, and by permitting withdrawl of the suctioning tube therefrom by hand with a resulting substantial resealing of said opening upon withdrawl of the tube without any further manipulation,
  whereby endotracheal suctioning may be periodically accomplished through the ventilator conduit without having to disconnect the patient from the respirator.

2. In a ventilator conduit adapted to be connected between a trachea tube and a respirator and having an opening in a side wall of said conduit near the trachea tube, the improvement comprising means installed in said opening for receiving a bendable suction tube therethrough for passage through said conduit into the trachea tube, said receiving means being characterized by substantially sealing said opening in the absence of the suction tube being positioned therein, by permitting insertion of the tube therethrough by pushing along its length in a manner to form a substantial seal between the tube and conduit without any further manipulation, and by permitting withdrawal of the suctioning tube therefrom by hand with a resulting substantial resealing of said opening upon withdrawal of the tube without any further manipulation, whereby endotracheal suctioning may be periodically accomplished through the ventilator conduit without having to disconnect the patient from the respirator.

3. The improved ventilator conduit according to claim 1, wherein said ventilator conduit includes a manifold having a first port extending substantially orthogonally to a portion of the conduit for connection of a tube thereto that is especially adapted for insertion in a trachea and at least one additional port for connecting a hose between the manifold and the respirator, said conduit side wall opening being located in a portion of the manifold wall opposite said first port.

4. The improved ventilator conduit according to claim 1, wherein said opening is oriented at an angle to a wall of the conduit in a manner that said suctioning tube enters through the opening in a direction substantially along the length of said conduit, said opening additionally being placed in a portion of the conduit, adapted to be positioned close to but outside of the patient.

5. The improved ventilator conduit according to claim 1, wherein said receiving means comprises a flexible resilient material being held across said opening and containing at least one slit therethrough capable of receiving the suctioning tube, said material normally holding said slit substantially closed without anything passed therethrough.

6. The improved ventilator conduit according to claim 1, wherein said receiving means comprise a plug of compressible material with an aperture therethrough and carried in said opening in a manner that said aperture is normally substantially closed but can receive said suctioning tube therethrough.

7. The improved ventilator conduit according to claim 1, wherein said tube is connected to a suctioning device through a valve that permits the tube to be opened and closed to fluid flow.

8. The improved ventilator conduit according to claim 1, wherein said opening is positioned in said wall at a bend at said conduit in a position substantially directly opposite a port that is adapted for connection to a tracheal tube.

9. The ventilator conduit according to any of claims 2, 3, 4 7 or 8 wherein said receiving means includes a substantially flat piece of resilient film held across said opening, said piece having an elongated slit therein that is normally held closed by the resiliency of material but which is openable by insertion of an end of said flexible tubing therethrough.

10. For use in a ventilator conduit adapted to be connected between a patient's trachea and a respirator, a manifold having a first opening for connection to a tracheal tube and second and third openings for connection to a respirator, the improvement comprising a fourth opening oriented generally opposite said first opening and formed of pre-punctured resilient material biased to normally maintain the puncture substantially closed but adapted to receive a tube therethrough and form a substantial seal therewith, whereby a suctioning tube may be selectively inserted through said fourth opening into a tracheal tube attached to the first opening of the manifold and removed therefrom while maintaining the integrity of an enclosed fluid passage within the manifold without any further manipulations being required.

11. For use in a ventilator conduit adapted to be connected between a patient's trachea and a respirator, a connector for joining a tracheal tube to a manifold in the vicinity of a patient's mouth, the connector comprising:
walls forming an enclosed gaseous passage having first and second openings therethrough shaped for connection with the tracheal tube and the manifold, respectively, and
a third opening in said wall formed of pre-punctured resilient material biased to normally maintain said puncture substantially closed but adapted to receive a bendable suctioning tube pushed along its length through said puncture and form a substantial seal around said tube, said third opening being positioned generally opposite said first opening,
whereby a suctioning tube may be selectively inserted through the third opening into a tracheal tube attached to the first opening of the connector and removed therefrom while maintaining the integrity of the enclosed gaseous passage without any further manipulations being required.

12. The connector according to claim 11 wherein each of said first and second openings are provided with first and second adapters, respectively, held by said connector in a manner to rotate with respect thereto about axes substantially orthogonal to each other and to form a substantial fluid tight seal therewith, said first and second adapters serving to provide the connection with the tracheal tube and manifold, respectively.

13. The ventilator conduit according to any of the claims 10, 11 or 12 wherein said pre-punctured resilient material includes a substantially flat piece of resilient film held across its said opening, that piece having an elongated slit therein that is normally closed by the resiliency of the material but which is openable by insertion of an end of said flexible tubing therethrough.

14. A ventilator assembly, comprising:
a pair of flexible hoses adapted at one end for connection to a respirator,
a trachea tube, and
means providing an enclosed conduit for connecting another end of said hoses to the trachea tube, said conduit including an opening in a wall thereof in which means are installed for receiving a bendable suction tube therethrough for entry into said conduit, said receiving means being characterized by substantially closing off said opening in the absence of the suction tube positioned therein, by permitting insertion of the suction tube therethrough by pushing along its length in a manner to form a substantial seal between the tube and conduit without any further manipulation, and by permitting withdrawal of the suctioning tube therefrom by hand with a resulting subtantial resealing of said opening upon withdrawal of the tube without any further manipulation, whereby endotracheal suctioning may be periodically accomplished through the ventilator conduit into the trachea tube without having to disconnect the patient from the respirator.

15. The ventilator assembly according to claim 11 wherein said opening is positioned in said wall at a bend of the conduit in a position substantially directly opposite said trachea tube, whereby the suction tube can be inserted substantially straight into said trachea tube.

16. The ventilator assembly according to claim 14 whereby said opening is oriented at an angle to a wall of the conduit in a manner that said suction tube enters through the opening in a direction substantially along the length of said conduit and into said trachea tube.

17. The ventilator assembly according to claim 14 wherein said conduit providing means includes a manifold with said opening in it.

18. The ventilator assembly according to claim 14, wherein said conduit providing means includes a manifold and a connector joining the manifold to the trachea tube, said opening being positioned in said connector.

19. The ventilator assembly according to any of claims 12, 14, 15, 16, 17 or 18, wherein said receiving means comprises a pre-punctured resilient material biased to normally maintain the puncture substantially closed but adapted to receive the suction tube therethrough and form a substantial seal therewith.

20. The ventilator assembly according to any of claims 14, 15, 16, 14 or 15 wherein said receiving means includes a substantially flat piece of resilient film held across said opening, said piece having an elongated slit therein that is normally held closed by the resiliency of the material but which is openable by insertion of an end of said flexible tubing therethrough.

21. A method of endotracheal suctioning of a breathing patient who is connected by a fluid conduit to a respirator from a tracheal oxygen tube, comprising the steps of:
  inserting one end of a length of bendable suctioning tube by pushing along its length through a pre-punctured resilient material provided in an opening in a wall of said conduit in order to provide a substantial fluid seal between the conduit and tube, thence into said tracheal tube until said one suctioning tube end extends out of said oxygen tube within the patient's trachea, said suctioning tube having an outside diameter significantly less than an inside diameter of said tracheal tube, and
  connecting another end of the suctioning tube to a suctioning apparatus, thereby to remove fluid from the patient, the inserting and connecting steps being accomplished with the respirator being operably connected to said tracheal tube, whereby suctioning is accomplished without interrupting the patient's breathing.

22. The method according to claim 21 which comprises, after suctioning is completed, the additional step of removing the suctioning tube from said conduit opening in a manner to cause said resilient material to reseal itself without any other manipulation being required, thereby to maintain the integrity of said conduit.

23. The method according to either of claims 21 or 22, wherein said respirator maintains positive end expiratory pressure within the patient's lungs during the steps of inserting and connecting.

24. A method of endotracheal suctioning of a breathing patient who is connected by a gaseous conduit from a tracheal oxygen tube to a respirator that maintains positive end expiratory pressure within lungs of the patient, comprising the steps of:
  providing an opening in said gaseous conduit near the tracheal tube which is normally substantially closed off by a pre-punctured resilient plug biased to normally maintain the puncture substantially closed,
  inserting one end of a suctioning tube through the puncture of said plug and thence into the patient's lungs through the tracheal tube, said plug by pushing along its length additionally characterized by forming a substantial seal around said suctioning tube when so inserted,
  suctioning the lungs of the patient to remove fluid therefrom through the suctioning tube, and
  removing the suctioning tube from said conduit through said plug once the suctioning is completed, whereby the resiliency of the plug again closes the puncture as the suctioning tube is removed, thereby to maintain positive end expiratory pressure during and after suctioning.

* * * * *

UNITED STATES PATENT AND TRADEMARK OFFICE
CERTIFICATE OF CORRECTION

PATENT NO. : 4,351,328
DATED : September 28, 1982
INVENTOR(S) : Balazs I. Bodai

It is certified that error appears in the above—identified patent and that said Letters Patent is hereby corrected as shown below:

```
Col. 4, line 26, change "52" to --51--.
Col. 4, line 37, change "it" to --is--.
```

In the Claims:

```
Col. 7, line 23, change "1" to --2--.
Col. 7, line 32, change "1" to --2--.
Col. 7, line 40, change "1" to --2--.
Col. 7, line 47, change "1" to --2--.
Col. 7, line 53, change "1" to --2--.
Col. 7, line 57, change "1" to --2--.
Col. 7, line 62, add a comma (,) after "4".
Col. 9, line 10, change "11" to --14--.
Col. 9, line 34, change "14" (second occurrence) to --17--,
                and change "15" (second occurrence) to --18--
Col. 10, line 33, before "suctioning" insert --bendable--.
Col. 10, line 34, after "plug" insert --by pushing along
                  its length--.
Col. 10, lines 35 and 36, delete "by pushing along its
                          length".
```

Signed and Sealed this

Thirtieth Day of August 1983

[SEAL]

Attest:

GERALD J. MOSSINGHOFF

Attesting Officer   Commissioner of Patents and Trademarks